United States Patent
Facchini et al.

(10) Patent No.: US 10,676,767 B2
(45) Date of Patent: Jun. 9, 2020

(54) METHODS AND COMPOSITIONS FOR MAKING EPHEDRINE AND RELATED ALKALOID COMPOUNDS

(71) Applicant: Willow BioSciences Inc., Calgary (CA)

(72) Inventors: Peter James Facchini, Calgary (CA); Jillian Hagel, Calgary (CA)

(73) Assignee: Willow BioSciences Inc., Calgary, Alberta (CA)

( * ) Notice: Subject to any disclaimer, the term of this patent is extended or adjusted under 35 U.S.C. 154(b) by 115 days.

(21) Appl. No.: 15/737,021

(22) PCT Filed: Jun. 22, 2016

(86) PCT No.: PCT/CA2016/050730
§ 371 (c)(1),
(2) Date: Dec. 15, 2017

(87) PCT Pub. No.: WO2016/205939
PCT Pub. Date: Dec. 29, 2016

(65) Prior Publication Data
US 2018/0179561 A1     Jun. 28, 2018

Related U.S. Application Data

(60) Provisional application No. 62/183,372, filed on Jun. 23, 2015.

(51) Int. Cl.
*C12P 13/00* (2006.01)
*C07C 213/08* (2006.01)
*C12N 9/10* (2006.01)

(52) U.S. Cl.
CPC .......... *C12P 13/001* (2013.01); *C07C 213/08* (2013.01); *C12N 9/1007* (2013.01); *C12Y 201/01* (2013.01)

(58) Field of Classification Search
None
See application file for complete search history.

(56) References Cited

U.S. PATENT DOCUMENTS 7,371,523 B1     5/2008   Thomae et al.

FOREIGN PATENT DOCUMENTS

WO    2015/181823    3/2015

OTHER PUBLICATIONS

Axelrod, Julius, "Purification and Properties of Phenylethanolamine-N-methyl Transferase", The Journal of Biological Chemistry, vol. 237, No. 5, p. 1657-1660 (1962).
Groves, Ryan A. et al., "Transcriptome Profiling of Khat (*Catha edulis*) and Ephedra sinica Reveals Gene Candidates Potentially Involved in Amphetamine-Type Alkaloid biosynthesis", PLoS ONE, Mar. 25, 2015, 10(3).
Grunewald, Gary L. et al. "Stereochemical Aspects of Phenylethanolamine Analogues as Substrates of Phenylethanolamine N-Methyltransferase", Journal of Medicinal Chemistry, vol. 31, p. 1984-1986 (1988).
Hagel et al., "Biosynthesis of Amphetamine Analogs in Plants", Trends in Plant Science, vol. 17, No. 7, p. 404-412 (Jul. 2012).
Krizevski et al., "Composition and stereochemistry of Ephedrine Alkaloids Accumulation in Ephedra sinica Stapf", Phytochemistry, vol. 71, p. 895-903 (2010).
Krizevski, R. et al. "Benzaldehyde is a precursor of phenylpropylamino alkaloids as revealed by targeted metabolic profiling and comparative biochemical analyses in Ephedra spp.", Phytochemistry, vol. 81, p. 71-79, 2012.
Lewinsohn, E. et al., "Biosynthesis of amphetamine-like alkaloids in Catha edulis and Ephedra spp., two distantly related taxa", 249th American Chemical Society National Meeting, Denver, Mar. 22-26, 2015. Conference paper, pp. 1, 27.
Database UniParc (online), N.N. "*Sesamum indicum* (oriental sesame)", Jan. 2015. Database accession No. UPI0005815759. XP-002787184.
Database UniParc (online), N.N. "*Brassica rapa* subsp. *pekinemsis* (Chinese cabbage)", Feb. 2012. Database accession No. UPI000254106D. XP-002787185.

*Primary Examiner* — Paul J Holland
(74) *Attorney, Agent, or Firm* — Bereskin & Parr LLP/S.E.N.C.R.L., s.r.l.; Micheline Gravelle

(57) ABSTRACT

Methods for making alkaloid compounds, including ephedrine and derivatives thereof. The methods involve the performance of an N-methyltransferase catalyzed chemical reaction.

17 Claims, 4 Drawing Sheets

Specification includes a Sequence Listing.

(1R, 2S)-norephedrine

FIG. 2A (1S, 2R)-pseudonorephedrine

FIG. 2B (1R, 2R)-norephedrine

FIG. 2C (1S, 2S)-pseudonorephedrine

FIG. 2D (1R, 2S)-ephedrine

FIG. 2E (1S, 2R)-pseudoephedrine

FIG. 2F (1R, 2R)-ephedrine

FIG. 2G (1S, 2S)-pseudoephedrine

FIG. 2H (1R, 2S)-N-methylephedrine

FIG. 2I (1S, 2R)-N-methylpseudoephedrine

FIG. 2J (1R, 2R)-N-methylephedrine

FIG. 2K (1S, 2S)-N-methylpseudoephedrine

FIG. 2L

SEQUENCE LISTING

<160> NUMBER OF SEQ ID NOS: 9

<210> SEQ ID NO 1
<211> LENGTH: 1490
<212> TYPE: DNA
<213> ORGANISM: Ephedra sinica

<400> SEQUENCE: 1

```
gctgaagctg tgaaccttac ttatggtgaa tattttgtca tttgtagtgt aatagctcgc      60
cgagtcgtta tccacaccaa gaaaatccaa atatacagta catgagtagc gactggatat     120
gttaggtgcc cacgaacact cctacaacat aatccacacg tagaatccca ttatgtagca     180
tcgactcatt catctaacgg agtctcaggt acacaaagaa ataagaacg aaagaatctg     240 aatggaagag gcgaagatgg caacgctggg cggtgcctcg tatgccatga tagtgaagac     300
aatgatgcgc tctctcgaag ccaacctaat tccggacttc gtactgagaa ggctcactcg     360
cattctcttg gcgagtcgtc tgaagctcgg atacaagcaa accgcggagc ttcagcttgc     420
tgatctcatg tcctttgttg catcgttaaa gaccatgcct atagctctct gcaccgaaga     480
agctaaaggc cagcattacg agctgcccac ttcgttcttc aagttggttc tcggcaagca     540
tctcaaatac agctcggctt acttcagtga acacacaaga actctagatg aagcagagga     600
agcaatgtta gcactgtatt gtgagagggc taagattgaa gatggccaaa agattctgga     660
tataggatgt ggatggggtt cattttcttt atatgttgct gaaagatacc caaaatgtga     720
aataactggt cttttgcaatt cctctaccca gaaggcgttt atagagcaac agtgcagtga     780
aagaagactt tgcaatgtta ctatatatgc tgatgatatt agcacttttg atacggagag     840
tacttatgat cgcataatat ctattgaaat gtttgagcac atgaaaaatt acagtactct     900
tcttaaaaaa atatcaaagt ggatgaatca ggaatgcttg ctgtttgtgc attattttg     960 tcataagaca tttgcttacc attttgagga tgtagatgaa gatgattgga tggcaagata    1020 cttttcaca ggtggcacaa tgcctgcaag tagcttacta ctgtatttc aggatgatgt    1080 ttcagttgtt gatcactggc ttataaatgg gaagcactat gctcaaacaa gtgaagagtg    1140
gctgaaaagg atggaccata atctatcctc tatacttcct atatttaatg aaacatatgg    1200
cgaaaatgca gctaaaaagt ggttggcata ctggcgaaca ttctttattg ccgtggctga    1260 gcttttaag tacaatgatg gagaagaatg gatggtttca cattttctgt ttaagaaaaa    1320
atagccacag catacctttt cgtatggtag aaagggtcgt tgattattgt aatttcttct    1380
```

```
attcttttcc atttgtgacc aatgctagtt aaatagtcaa acaaatttct ctagcataga   1440
ttttgaaggt taatatttca gaattccaca aaatttctct atgaggattt              1490
```

<210> SEQ ID NO 2
<211> LENGTH: 1083
<212> TYPE: DNA
<213> ORGANISM: Ephedra sinica

<400> SEQUENCE: 2

```
atggaagaag caaaaatggc gaccctgggc ggtgcgtcct atgcgatgat tgtgaaaacg     60
atgatgcgct ctctggaagc aaacctgatt ccggattttg tgctgcgtcg cctgacgcgt    120
atcctgctgg ctagtcgcct gaaactgggt tataagcaga ccgctgaact gcaactggcg    180
gatctgatgt cattcgttgc gtcgctgaaa acgatgccga ttgccctgtg caccgaagaa    240
gcaaagggtc agcattacga actgccgacc agcttttttca aactggtcct gggcaaacat    300
ctgaagtata gctctgccta cttttctgaa cacaccgta cgctggatga agcggaagaa    360
gccatgctgg cactgtattg cgaacgcgcc aaaattgaag atggtcagaa gattctggac    420
atcggctgtg gttggggcag ttttttccctg tatgtggcag aacgttaccc gaaatgcgaa    480
attacgggcc tgtgtaacag ttccacccaa aaagccttca tcgaacagca atgcagcgaa    540
cgtcgcctgt gtaatgttac catttatgca gatgacatca gcacctttga tacggaatct    600
acctacgacc gcattatcag catcgaaatg ttcgaacaca tgaagaacta cagtacgctg    660
ctgaagaaaa ttagcaagtg gatgaatcag gaatgcctgc tgtttgtcca ttatttctgt    720
cacaaaacct ttgcgtacca cttcgaagat gtggacgaag atgactggat ggctcgttat    780
ttctttaccg gcggcaccat gccggcgtca tcgctgctgc tgtactttca ggatgacgtc    840
tcagtggttg atcattggct gattaacggt aaacactatg ctcaaacctc ggaagaatgg    900
ctgaagcgta tggaccacaa tctgagctct attctgccga tctttaacga aacgtatggc    960
gaaaatgcgg ccaaaaagtg gctggcatac tggcgcacct ttttcatcgc agttgctgaa   1020
ctgttcaaat acaacgatgg cgaagaatgg atggtgtccc acttcctgtt caaaagaaaa   1080
taa                                                                 1083
```

<210> SEQ ID NO 3
<211> LENGTH: 360
<212> TYPE: PRT
<213> ORGANISM: Ephedra sinica

<400> SEQUENCE: 3

```
Met Glu Glu Ala Lys Met Ala Thr Leu Gly Gly Ala Ser Tyr Ala Met
1               5                   10                  15

Ile Val Lys Thr Met Met Arg Ser Leu Glu Ala Asn Leu Ile Pro Asp
            20                  25                  30

Phe Val Leu Arg Arg Leu Thr Arg Ile Leu Leu Ala Ser Arg Leu Lys
        35                  40                  45

Leu Gly Tyr Lys Gln Thr Ala Glu Leu Gln Leu Ala Asp Leu Met Ser
    50                  55                  60

Phe Val Ala Ser Leu Lys Thr Met Pro Ile Ala Leu Cys Thr Glu Glu
65                  70                  75                  80

Ala Lys Gly Gln His Tyr Glu Leu Pro Thr Ser Phe Phe Lys Leu Val
                85                  90                  95

Leu Gly Lys His Leu Lys Tyr Ser Ser Ala Tyr Phe Ser Glu His Thr
            100                 105                 110
```

```
Arg Thr Leu Asp Glu Ala Glu Ala Met Leu Ala Leu Tyr Cys Glu
            115                 120                 125
Arg Ala Lys Ile Glu Asp Gly Gln Lys Ile Leu Asp Ile Gly Cys Gly
        130                 135                 140
Trp Gly Ser Phe Ser Leu Tyr Val Ala Glu Arg Tyr Pro Lys Cys Glu
145                 150                 155                 160
Ile Thr Gly Leu Cys Asn Ser Ser Thr Gln Lys Ala Phe Ile Glu Gln
                165                 170                 175
Gln Cys Ser Glu Arg Arg Leu Cys Asn Val Thr Ile Tyr Ala Asp Asp
            180                 185                 190
Ile Ser Thr Phe Asp Thr Glu Ser Thr Tyr Asp Arg Ile Ile Ser Ile
        195                 200                 205
Glu Met Phe Glu His Met Lys Asn Tyr Ser Thr Leu Leu Lys Lys Ile
    210                 215                 220
Ser Lys Trp Met Asn Gln Glu Cys Leu Leu Phe Val His Tyr Phe Cys
225                 230                 235                 240
His Lys Thr Phe Ala Tyr His Phe Glu Asp Val Asp Glu Asp Trp
                245                 250                 255
Met Ala Arg Tyr Phe Phe Thr Gly Gly Thr Met Pro Ala Ser Ser Leu
            260                 265                 270
Leu Leu Tyr Phe Gln Asp Asp Val Ser Val Val Asp His Trp Leu Ile
        275                 280                 285
Asn Gly Lys His Tyr Ala Gln Thr Ser Glu Glu Trp Leu Lys Arg Met
    290                 295                 300
Asp His Asn Leu Ser Ser Ile Leu Pro Ile Phe Asn Glu Thr Tyr Gly
305                 310                 315                 320
Glu Asn Ala Ala Lys Lys Trp Leu Ala Tyr Trp Arg Thr Phe Phe Ile
                325                 330                 335
Ala Val Ala Glu Leu Phe Lys Tyr Asn Asp Gly Glu Glu Trp Met Val
            340                 345                 350
Ser His Phe Leu Phe Lys Lys Lys
        355                 360

<210> SEQ ID NO 4
<211> LENGTH: 1092
<212> TYPE: DNA
<213> ORGANISM: Sesamum indicum

<400> SEQUENCE: 4
atggcggagg ttaacggccg catcatcgat accattgtgc agatgcccta cgacgcaacc      60
gtacgtttta tgcttgcttc tctcgagcgc aacttgctgc ctgacgccgt tgtgcgccgc     120
ctcactcgtc tgcttctcgc tagtcgcctc cgctcaggat acagatcctc cgcggaactc     180
cagttgtccg acctccttca atttgcgcat tctttgagag aaatgccaat agcaatcaag     240
acggaaaagc caaagtctca gcactatgaa gttccaacgt cttacttcaa gcttgtcctt     300
ggaaagcatt taaaatacag ctgctgcttc tttcccaaca gtcgagcac cttagaggat     360
gctgagaagg caatgctaga gttatactgt gagaggtcac agataaaaga tggtcaatca     420
gtccttgatg ttggttgtgg ctggggatct ctttctatat acatagcaca gaagtacccc     480
aattgccagg ttacggggat tgcaattca ataacccaga aagcacatat tgaggagcag     540
tgccgggaac ttcagttgca gaatgtggag ataattgtag cagatatcag cacatttgac     600
atggaagctt catatgacag aatatttcc attgaaatgt ttgagcatat gaaaaactat     660
caggatcttc ttaagaagat atcgaagtgg atgaaaccag acagttttct gtttgtccat     720
```

```
tatttttgcc ataaaacatt tgcttaccac tttgaggacg taaatgagga cgactggatc     780
actaggtact tctttactgg aggtacaatg ccttctgcaa acctgctcct ttattttcag     840
gacgatgtgt ctatagttaa tcattggctt gtgaacggca agcattatgc acagacaagc     900
gaggaatggc ttaagagaat ggaccagaac ttgaattcta taaagccaat aatggaatgc     960
acttatggca agattcagc ggtcaaatgg acagtctact ggagaacatt tttcattgca    1020
gttgcagaat tatttggcta caacaatgga gaagagtgga tggttgctca tttcctttc    1080 aagaagaaat aa                                                       1092
```

<210> SEQ ID NO 5
<211> LENGTH: 363
<212> TYPE: PRT
<213> ORGANISM: Sesamum indicum

<400> SEQUENCE: 5

```
Met Ala Glu Val Asn Gly Arg Ile Ile Asp Thr Ile Val Gln Met Pro
1               5                   10                  15

Tyr Asp Ala Thr Val Arg Phe Met Leu Ala Ser Leu Glu Arg Asn Leu
            20                  25                  30

Leu Pro Asp Ala Val Arg Arg Leu Thr Arg Leu Leu Leu Ala Ser
        35                  40                  45

Arg Leu Arg Ser Gly Tyr Arg Ser Ser Ala Glu Leu Gln Leu Ser Asp
    50                  55                  60

Leu Leu Gln Phe Ala His Ser Leu Arg Glu Met Pro Ile Ala Ile Lys
65                  70                  75                  80

Thr Glu Lys Pro Lys Ser Gln His Tyr Glu Val Pro Thr Ser Tyr Phe
                85                  90                  95

Lys Leu Val Leu Gly Lys His Leu Lys Tyr Ser Cys Cys Phe Phe Pro
            100                 105                 110

Asn Lys Ser Ser Thr Leu Glu Asp Ala Glu Lys Ala Met Leu Glu Leu
        115                 120                 125

Tyr Cys Glu Arg Ser Gln Ile Lys Asp Gly Gln Ser Val Leu Asp Val
    130                 135                 140

Gly Cys Gly Trp Gly Ser Leu Ser Ile Tyr Ile Ala Gln Lys Tyr Pro
145                 150                 155                 160

Asn Cys Gln Val Thr Gly Ile Cys Asn Ser Ile Thr Gln Lys Ala His
                165                 170                 175

Ile Glu Glu Gln Cys Arg Glu Leu Gln Leu Gln Asn Val Glu Ile Ile
            180                 185                 190

Val Ala Asp Ile Ser Thr Phe Asp Met Glu Ala Ser Tyr Asp Arg Ile
        195                 200                 205

Phe Ser Ile Glu Met Phe Glu His Met Lys Asn Tyr Gln Asp Leu Leu
    210                 215                 220

Lys Lys Ile Ser Lys Trp Met Lys Pro Asp Ser Phe Leu Phe Val His
225                 230                 235                 240

Tyr Phe Cys His Lys Thr Phe Ala Tyr His Phe Glu Asp Val Asn Glu
                245                 250                 255

Asp Asp Trp Ile Thr Arg Tyr Phe Phe Thr Gly Gly Thr Met Pro Ser
            260                 265                 270

Ala Asn Leu Leu Leu Tyr Phe Gln Asp Asp Val Ser Ile Val Asn His
        275                 280                 285

Trp Leu Val Asn Gly Lys His Tyr Ala Gln Thr Ser Glu Glu Trp Leu
    290                 295                 300
```

```
Lys Arg Met Asp Gln Asn Leu Asn Ser Ile Lys Pro Ile Met Glu Cys
305                 310                 315                 320

Thr Tyr Gly Lys Asp Ser Ala Val Lys Trp Thr Val Tyr Trp Arg Thr
            325                 330                 335

Phe Phe Ile Ala Val Ala Glu Leu Phe Gly Tyr Asn Asn Gly Glu Glu
        340                 345                 350

Trp Met Val Ala His Phe Leu Phe Lys Lys Lys
        355                 360
```

```
<210> SEQ ID NO 6
<211> LENGTH: 1068
<212> TYPE: DNA
<213> ORGANISM: Brassica rapus

<400> SEQUENCE: 6
```

```
atggagagga ttgtcgaggt agcttatgga gcatccgtga aagcagtttt aacgttgttg    60
gagaagaatc tgctgccgga tgttgtcata aggctactaa cgcggctgct tctcgccggt   120
cgacttcgtt ccggttacaa acccacggcg gagctgcaac tttctgatct actccgtttc   180
gttaactcta taaagagat gcctatagca ataaatactg agaagccgaa gacgcaacac   240
tatgaattac caaccgcttt cttcgaactt gttcttggaa gaaacatgaa atacagctca   300
tgttatttcc caaggattc aagttgctta gaagaagcag aggaagcaat attggctcta   360
tattgcgaaa gagctaaagt ggaagatgga caaagtgttc tcgatgtcgg atgtggctgg   420
ggatctttgt ctttgtacat tgcccgcaag tatatcaatt gcaagttaac cggtctttgc   480
aactcaaaaa cacagaaagc atttatcgat gaccaatgca ggaaacttgg cattcaaaat   540
gtcgaaatca ttgttgggga taatagcact tttgagcatg aagggacata tgaccgagtg   600
ttctccatcg aaatgtttga gcatatgaaa actatggag agcttctgaa gaaaattgga   660
agctggatga gggaagatag tcttctgttt gttcactatt tctgccataa gacatttgct   720
taccattttg aggatgtgca tgacgatgac tggatcacaa gatacttctt agtggagga   780
acaatgccat cggcgaatct tctcctctat ttccaagacg atgtttcgat gtgggatcat   840
tggctcctaa acgggaagca ttatgcaagg accagtgagg agtggctcaa agaatggac   900
aaggagatag ttgcaataaa ggagataatg gaaatgactt atgggaaga ggaggcagtg   960
aagtggatgg tttactggag aaccttcttc atggcggttg ctgagctttt tggatacaac  1020
aatggagaag agtggatgat ttcacacttc ttattcaaga gaaaatga                1068
```

```
<210> SEQ ID NO 7
<211> LENGTH: 355
<212> TYPE: PRT
<213> ORGANISM: Brassica rapus

<400> SEQUENCE: 7
```

```
Met Glu Arg Ile Val Glu Val Ala Tyr Gly Ala Ser Val Lys Ala Val
1               5                   10                  15

Leu Thr Leu Leu Glu Lys Asn Leu Leu Pro Asp Val Val Ile Arg Leu
            20                  25                  30

Leu Thr Arg Leu Leu Leu Ala Gly Arg Leu Arg Ser Gly Tyr Lys Pro
        35                  40                  45

Thr Ala Glu Leu Gln Leu Ser Asp Leu Leu Arg Phe Val Asn Ser Ile
    50                  55                  60

Lys Glu Met Pro Ile Ala Ile Asn Thr Glu Lys Pro Lys Thr Gln His
65                  70                  75                  80
```

Tyr Glu Leu Pro Thr Ala Phe Phe Glu Leu Val Leu Gly Arg Asn Met
            85                  90                  95

Lys Tyr Ser Ser Cys Tyr Phe Pro Lys Asp Ser Ser Cys Leu Glu Glu
        100                 105                 110

Ala Glu Glu Ala Ile Leu Ala Leu Tyr Cys Glu Arg Ala Lys Val Glu
        115                 120                 125

Asp Gly Gln Ser Val Leu Asp Val Gly Cys Gly Trp Gly Ser Leu Ser
    130                 135                 140

Leu Tyr Ile Ala Arg Lys Tyr Ile Asn Cys Lys Leu Thr Gly Leu Cys
145                 150                 155                 160

Asn Ser Lys Thr Gln Lys Ala Phe Ile Asp Asp Gln Cys Arg Lys Leu
            165                 170                 175

Gly Ile Gln Asn Val Glu Ile Ile Val Gly Asp Asn Ser Thr Phe Glu
        180                 185                 190

His Glu Gly Thr Tyr Asp Arg Val Phe Ser Ile Glu Met Phe Glu His
    195                 200                 205

Met Lys Asn Tyr Gly Glu Leu Leu Lys Lys Ile Gly Ser Trp Met Arg
    210                 215                 220

Glu Asp Ser Leu Leu Phe Val His Tyr Phe Cys His Lys Thr Phe Ala
225                 230                 235                 240

Tyr His Phe Glu Asp Val His Asp Asp Trp Ile Thr Arg Tyr Phe
            245                 250                 255

Phe Ser Gly Gly Thr Met Pro Ser Ala Asn Leu Leu Leu Tyr Phe Gln
        260                 265                 270

Asp Asp Val Ser Ile Val Asp His Trp Leu Leu Asn Gly Lys His Tyr
    275                 280                 285

Ala Arg Thr Ser Glu Glu Trp Leu Lys Arg Met Asp Lys Glu Ile Val
    290                 295                 300

Ala Ile Lys Glu Ile Met Glu Met Thr Tyr Gly Lys Glu Glu Ala Val
305                 310                 315                 320

Lys Trp Met Val Tyr Trp Arg Thr Phe Phe Met Ala Val Ala Glu Leu
            325                 330                 335

Phe Gly Tyr Asn Asn Gly Glu Glu Trp Met Ile Ser His Phe Leu Phe
        340                 345                 350

Lys Lys Lys
    355

<210> SEQ ID NO 8
<211> LENGTH: 1161
<212> TYPE: DNA
<213> ORGANISM: Erythranthe guttata

<400> SEQUENCE: 8
atgctgaaag ataaatcaca gcgaaaatac gcaactccgt catcttcagc tgacgattcc      60
acggtaacaa tggcggcagt taacggcggc attgtggatt cgattgtcca ggtgccctac     120
gaggccaccg tacgcctcat gctcggttcg ctcgagcgga atctgttgcc cgacgccgtc     180
gtgcgccgcc tcactcggct ccttctcgcc agtcgcctcc gctccggtta cagatcctcc     240
gccgacatcc agctgtccga tctcctcaat tttgtgcatt ctttgaaaga atgccgata      300 gcaatccaga cagaaacgcc aaagtctcaa cattacgaag ttcctacatc tttcttcaag     360
cttgccctcg gcaaacatct caaatacagt tgctgctatt tttcagataa gtcaagcact     420
ttagacgatg ccgagaaggc aatgcttgag ttgtactgtg agagatcgca gataaaagac     480

-continued

```
ggtcattccg ttctcgatgt cggttgtggc tggggatctc tttccctata cattgctcag    540
aaataccccca attgcctgat caaagggatt tgcaattcca ttacccaaaa ggaacacatc    600
gaggagcagt gtcgggatct tcaagtaaag aatgtggaga tagttgttgg agatatcagc    660
acgtttgata tggaagcttc ttatgacaga atatttttcca ttgaaatgtt tgagcatatg    720
aaaaactacc gtgatcttct taagaagata tccaagtgga tgaaatcgga cggtcttctg    780
ttcatccatt atttctgcca taaaacattt gcttaccact ttgaggatgt caacgaggac    840
gattggatca ctaggtactt ctttactgga ggtacaatgc cctcagcaga cctgctcctt    900
tactttcagg atgacgtttc tatagtcgat cactggcttg tgaatggcaa gcattatgca    960
cagacaagtg aagaatggct taagagaatg daccagaatt tgagctcaat aaagccatta   1020
atggagtcca cttatggtaa agattcagct gtcaagtgga ccgtctattg agaacatttt   1080
tcattgcgg ttgcggaatt gttcggctac aacaatggag aagaatggat ggttgctcat   1140
ttccttttca agaagaaata a                                             1161
```

<210> SEQ ID NO 9
<211> LENGTH: 386
<212> TYPE: PRT
<213> ORGANISM: Erythranthe guttata

<400> SEQUENCE: 9

```
Met Leu Lys Asp Lys Ser Gln Arg Lys Tyr Ala Thr Pro Ser Ser Ser
1               5                   10                  15

Ala Asp Asp Ser Thr Val Thr Met Ala Ala Val Asn Gly Gly Ile Val
            20                  25                  30

Asp Ser Ile Val Gln Val Pro Tyr Glu Ala Thr Val Arg Leu Met Leu
        35                  40                  45

Gly Ser Leu Glu Arg Asn Leu Leu Pro Asp Ala Val Val Arg Arg Leu
    50                  55                  60

Thr Arg Leu Leu Leu Ala Ser Arg Leu Arg Ser Gly Tyr Arg Ser Ser
65                  70                  75                  80

Ala Asp Ile Gln Leu Ser Asp Leu Leu Asn Phe Val His Ser Leu Lys
                85                  90                  95

Glu Met Pro Ile Ala Ile Gln Thr Glu Thr Pro Lys Ser Gln His Tyr
            100                 105                 110

Glu Val Pro Thr Ser Phe Phe Lys Leu Ala Leu Gly Lys His Leu Lys
        115                 120                 125

Tyr Ser Cys Cys Tyr Phe Ser Asp Lys Ser Ser Thr Leu Asp Asp Ala
    130                 135                 140

Glu Lys Ala Met Leu Glu Leu Tyr Cys Glu Arg Ser Gln Ile Lys Asp
145                 150                 155                 160

Gly His Ser Val Leu Asp Val Gly Cys Gly Trp Gly Ser Leu Ser Leu
                165                 170                 175

Tyr Ile Ala Gln Lys Tyr Pro Asn Cys Leu Ile Lys Gly Ile Cys Asn
            180                 185                 190

Ser Ile Thr Gln Lys Glu His Ile Glu Glu Gln Cys Arg Asp Leu Gln
        195                 200                 205

Val Lys Asn Val Glu Ile Val Val Gly Asp Ile Ser Thr Phe Asp Met
    210                 215                 220

Glu Ala Ser Tyr Asp Arg Ile Phe Ser Ile Glu Met Phe Glu His Met
225                 230                 235                 240

Lys Asn Tyr Arg Asp Leu Leu Lys Lys Ile Ser Lys Trp Met Lys Ser
                245                 250                 255
```

```
Asp Gly Leu Leu Phe Ile His Tyr Phe Cys His Lys Thr Phe Ala Tyr
            260                 265                 270

His Phe Glu Asp Val Asn Glu Asp Asp Trp Ile Thr Arg Tyr Phe Phe
        275                 280                 285

Thr Gly Gly Thr Met Pro Ser Ala Asp Leu Leu Leu Tyr Phe Gln Asp
        290                 295                 300

Asp Val Ser Ile Val Asp His Trp Leu Val Asn Gly Lys His Tyr Ala
305                 310                 315                 320

Gln Thr Ser Glu Glu Trp Leu Lys Arg Met Asp Gln Asn Leu Ser Ser
                325                 330                 335

Ile Lys Pro Leu Met Glu Ser Thr Tyr Gly Lys Asp Ser Ala Val Lys
            340                 345                 350

Trp Thr Val Tyr Trp Arg Thr Phe Phe Ile Ala Val Ala Glu Leu Phe
            355                 360                 365

Gly Tyr Asn Asn Gly Glu Glu Trp Met Val Ala His Phe Leu Phe Lys
        370                 375                 380

Lys Lys
385
```

METHODS AND COMPOSITIONS FOR MAKING EPHEDRINE AND RELATED ALKALOID COMPOUNDS

RELATED APPLICATION

This application is a national phase entry application of Patent Cooperation Treaty Application No. PCT/CA2016/050730, filed Jun. 22, 2018 (which designates the U.S.), which claims the benefit under 35 USC § 119(e) from U.S. Provisional Application No. 62/183,372, filed on Jun. 23, 2015, which are incorporated herein by reference in their entirety.

Incorporation of Sequence Listing

A computer readable form of the Sequence Listing "21806-P48792US01_SequenceListing.txt" (24,576 bytes), submitted via EFS-WEB and created on Dec. 14, 2017, is herein incorporated by reference.

FIELD OF THE DISCLOSURE

The present disclosure relates to methods for making alkaloid compounds, notably ephedrine.

BACKGROUND OF THE DISCLOSURE

The following paragraphs are provided by way of background to the present disclosure. They are not however an admission that anything discussed therein is prior art or part of the knowledge of persons skilled in the art.

The pharmacological properties of ephedrine and related alkaloid compounds have long been recognized. Thus ephedrine may be used inter alia as a decongestant, stimulant, concentration aid, and appetite suppressant. In order to prepare pharmaceutical formulations, ephedrine may be extracted from natural sources, including plant species belonging to the genus *Catha*, *Catha edulis*, for example, and plant species belonging to the genus *Ephedra*, *Ephedra sinica*, for example. However yields of plant-extracted ephedrine are typically modest (Shukla et al., 2000, World J. Biotechn. 16: 499-506). In practice, plant extracts are commonly used for the preparation of herbal formulations and supplements containing ephedrine. Plant extraction processes, due to their limited efficiency, are less suitable for the large-scale manufacture of substantially pure ephedrine. Ephedrine may also be produced chemically for example by condensing 1-phenyl-1,2-propanedione with methylamine, providing racemic mixtures of ephedrine (Manske and Johnson, 1929, Am. Chem. Soc. 51: 580-582), or from propionic acid (Feldman et al., 1962, J. Appl. Chem. 35, 1309-1311). In general, chemical production of ephedrine is cumbersome as it involves the use of several substantially pure chemical compounds, which are not necessarily available on suitably economic terms and multistep preparation processes. Moreover only limited enantiomeric purity is attainable through chemical synthesis, i.e. the chemical synthesis processes yield a mixture of (R)- and (S)-enantiomers. It is noted in this regard that different ephedrine enantiomers exhibit different pharmacological properties. Thus the currently most commonly used process for commercial bulk manufacturing of ephedrine consists of two separate steps, an initial biosynthetic production step, followed by a chemical synthesis step. Notably, this process involves fermentation of sugars in yeast in the presence of benzaldehyde, an inexpensive additive, resulting in the production of (R)-phenylacetylcarbinol, also known as (R)-PAC. This precursor compound is subsequently used to produce ephedrine by the performance of a chemical reductive amination reaction.

Despite the well-understood chemistry relating to the synthesis of ephedrine and related alkaloid compounds, it was heretofore unknown whether and how de novo biosynthetic production of ephedrine may be achieved. Such biosynthetic production system is desirable as it represents a large scale economical production process for substantially pure ephedrine and related alkaloid compounds using a one-step process, obviating the need for a chemical synthesis step converting (R)-PAC to ephedrine, as is required to operate the currently used commercial production systems for ephedrine.

There exists therefore a need in the art for improved methods for the production of ephedrine and related alkaloid compounds.

SUMMARY OF THE DISCLOSURE

The following paragraphs are intended to introduce the reader to the more detailed description that follows and not to define or limit the claimed subject matter of the present disclosure.

In one aspect, the present disclosure relates to ephedrine and related alkaloid compounds.

In one aspect, the present disclosure relates to N-methyltransferases.

Accordingly, the present disclosure provides, in at least one implementation, a method of making an alkaloid compound having a chemical formula (II):

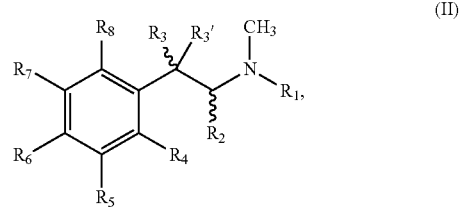

the method comprising
providing an alkaloid compound having a chemical formula (I):

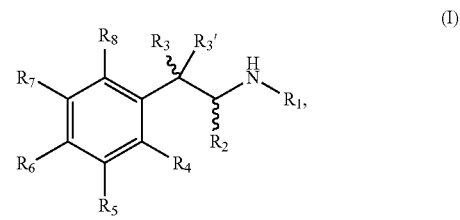

contacting the alkaloid compound having a chemical formula (I) with sufficient quantities of a methyl-donor and a catalytic quantity of an N-methyl-transferase under reaction conditions permitting an enzyme catalyzed conversion of the alkaloid compound having chemical formula (I) to an alkaloid compound having chemical formula (II).

In some implementations, in the alkaloid compound having chemical formula (I) $R_1$ is a hydrogen atom, a methyl group or a halogen; $R_2$ is a hydrogen atom, a methyl group or a methoxy group; $R_3$ is a hydroxyl group, or a halogen, $R_3'$ is a hydrogen atom, or taken together $R_3$ and $R_3'$ form a carbonyl group (C=O); $R_4$-$R_8$ are each independently or simultaneously a hydrogen atom, methyl group, hydroxyl group, halogen or methoxy group; and each $R_1$ to $R_8$ and $R_3'$ in the alkaloid compound having chemical formula (I) are identical to $R_1$ to $R_8$ and $R_3'$ in the alkaloid compound having chemical formula (II).

In some implementations, in both the alkaloid compound having chemical formula (I) and the alkaloid compound having chemical formula (II), $R_1$ is a hydrogen atom, $R_2$ is a methyl group, $R_3$ is a hydroxyl group, $R_3'$ is a hydrogen atom and $R_4$-$R_8$ are hydrogen atoms. It is noted that in such implementations, the alkaloid compound having chemical formula (I) is also referred to as norephedrine and the alkaloid compound having chemical formula (II) is also referred to as ephedrine.

In some implementations, in both the alkaloid compound having chemical formula (I) and the alkaloid compound having chemical formula (II) $R_1$ is a methyl group, $R_2$ is a methyl group, $R_3$ is a hydroxyl group, $R_3'$ is a hydrogen atom and $R_4$-$R_8$ are hydrogen atoms. It is noted that in such implementations, the alkaloid compound having chemical formula (I) is also referred to as ephedrine and the alkaloid compound having chemical formula (II) is also referred to as N-methylephedrine.

In some implementations, $R_2$ is spatially oriented so that the alkaloid compound having a chemical formula (I) or (II) is a 2R-enantiomer.

In some implementations, $R_2$ is spatially oriented so that the alkaloid compound having a chemical formula (I) or (II) is a 2S-enantiomer.

In some implementations, $R_3$ is spatially oriented so that the alkaloid compound having a chemical formula (I) or (II) is a 1R-enantiomer.

In some implementations, $R_3$ is spatially oriented so that the alkaloid compound having a chemical formula (I) or (II) is a 1S-enantiomer.

In some implementations, the alkaloid compound having chemical formula (I) is (1S, 2S)-pseudonorephedrine and the alkaloid compound having chemical formula (II) is (1S, 2S)-pseudoephedrine.

In some implementations, the alkaloid compound having chemical formula (I) is (1R, 2R)-norephedrine and the alkaloid compound having chemical formula (II) is (1R, 2R)-ephedrine.

In some implementations, the alkaloid compound having chemical formula (I) is (1R, 2S)-norephedrine and the alkaloid compound having chemical formula (II) is (1R, 2S)-ephedrine.

In some implementations, the alkaloid compound having chemical formula (I) is (1S, 2R)-pseudonorephedrine and the alkaloid compound having chemical formula (II) is (1S, 2R)-pseudoephedrine.

In some implementations, the alkaloid compound having chemical formula (I) is (1S, 2S)-pseudoephedrine and the alkaloid compound having chemical formula (II) is (1S, 2S)—N-methyl-pseudoephedrine.

In some implementations, the alkaloid compound having chemical formula (I) is (1R, 2R)-ephedrine and the alkaloid compound having chemical formula (II) is (1R, 2R)—N-methyl-ephedrine.

In some implementations, the alkaloid compound having chemical formula (I) is (1R, 2S)-ephedrine and the alkaloid compound having chemical formula (II) is (1R, 2S)—N-methyl-ephedrine.

In some implementations, the alkaloid compound having chemical formula (I) is (1S, 2R)-pseudoephedrine and the alkaloid compound having chemical formula (II) is (1S, 2R)—N-methyl-pseudoephedrine.

In some implementations, in both the alkaloid compound having chemical formula (I) and (II) $R_1$, and $R_4$-$R_8$ are each hydrogen atoms, $R_2$ is a methyl group, and, taken together, $R_3$ and $R_3'$ form a carbonyl group (C=O). It is noted that the compound having chemical formula (I) is known as cathinone, and the compound having chemical formula (II) is known as methcathinone.

In some implementations, in both the alkaloid compound having chemical formula (I) and (II), $R_1$, $R_2$, $R_3'$, $R_4$, $R_5$, $R_7$ and $R_8$ are each hydrogen atoms, and $R_3$ and $R_6$ are hydroxyl groups. It is noted that the compound having chemical formula (I) is known as p-octopamine, and the compound having chemical formula (II) is known as synephrine.

In some implementations, in both the alkaloid compound having chemical formula (I) and (II), $R_1$ is a methyl group, $R_2$, $R_3'$, $R_4$, $R_5$, $R_6$ and $R_8$ are each hydrogen atoms, and $R_3$ and $R_7$ are hydroxyl groups. It is noted that the compound having chemical formula (I) is known as N-desmethylphenylephrine, and the compound having chemical formula (II) is known as phenylephrine.

In some implementations, in both the alkaloid compound having chemical formula (I) and (II), $R_1$ is a methyl group, $R_2$, $R_3'$, $R_4$, $R_5$, $R_7$ and $R_8$ are each hydrogen atoms, and $R_3$ and $R_6$ are hydroxyl groups. It is noted that the compound having chemical formula (I) is known as synephrine, and the compound having chemical formula (II) is known as N-methyl-synephrine.

In some implementations, the N-methyl-transferase is obtained or obtainable from a plant species belonging to the genus *Catha* or from a plant belonging to the genus *Ephedra*.

In some implementations, the methods disclosed herein are conducted in vivo.

In some implementations, the methods disclosed herein are conducted in vitro.

Other features and advantages of the present disclosure will become apparent from the detailed description. It should be understood, however, that the detailed description, while indicating preferred implementations of the disclosure, are given by way of illustration only, since various changes and modifications within the spirit and scope of the disclosure will become apparent to those of skill in the art of the detailed description.

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

FIG. 2 depicts the chemical structures of various stereoisomers of norephedrine (FIG. 2A-FIG. 2D), ephedrine (FIG. 2E-FIG. 2H), and N-methylephedrine (FIG. 2I-FIG. 2L).

DETAILED DESCRIPTION OF THE DISCLOSURE

Various compositions and methods will be described below to provide an example of an embodiment of each claimed subject matter. No embodiment described below limits any claimed subject matter and any claimed subject matter may cover methods, processes, compositions or systems that differ from those described below. The claimed subject matter is not limited to compositions or methods having all of the features of any one composition, method, system or process described below or to features common to multiple or all of the compositions, systems or methods described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

As hereinbefore mentioned, the present disclosure relates to processes for the production of ephedrine and certain related alkaloid compounds. The herein provided processes are novel and provide, for the first time, a means permitting de novo biosynthetic production at commercial scale of ephedrine and related alkaloid compounds, obviating the need for a chemical synthetic step using a precursor compound. The obtained compounds of present disclosure are useful inter alia in the manufacture of pharmaceutical compositions.

Terms and Definitions

Figure 1A:
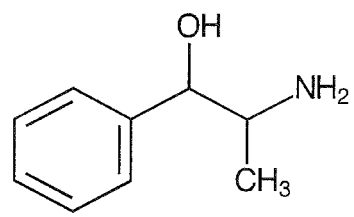
FIG. 1 depicts the chemical structures of certain alkaloid chemical compounds having the general chemical formula (I) or (II).

The term "norephedrine", as used herein, refers to the compound shown in FIG. 1A. It is noted that the term norephedrine, unless specifically used in conjunction with stereoisomer notation (e.g. (1R, 2S)-norephedrine), is intended to include all 4 stereoisomers of ephedrine, i.e. (1R, 2S)-norephedrine, (1S, 2R)-pseudonorephedrine, (1R, 2R)-norephedrine and (1S, 2S)-pseudonorephedrine.

Figure 1B:
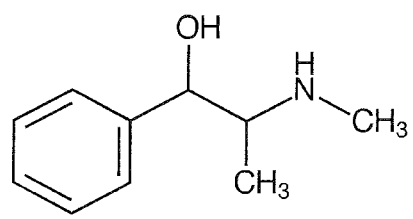

The term "ephedrine", as used herein, refers to the compound shown in FIG. 1B. It is noted that the term ephedrine, unless specifically used in conjunction with stereoisomer notation (e.g. (1R, 2S)-ephedrine), is intended to include all 4 stereoisomers of ephedrine, i.e. (1R, 2S)-ephedrine, (1S, 2R)-pseudoephedrine, (1R, 2R)-ephedrine and (1S, 2S)-pseudoephedrine.

Figure 1C:
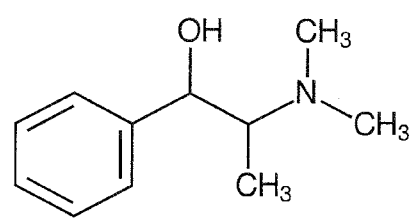

The term "N-methylephedrine" as used herein refers to the compound shown in FIG. 1C. It is noted that the term N-methylephedrine, unless specifically used in conjunction with stereoisomer notation (e.g. (1R, 2S)—N-methylephedrine), is intended to include all 4 stereoisomers of ephedrine, i.e. (1R, 2S)—N-methylephedrine, (1S, 2R)—N-methylpseudoephedrine, (1R, 2R)—N-methylephedrine and (1S, 2S)—N-methylpseudoephedrine.

The term "(1R, 2S)-norephedrine", as used herein refers to the chemical compound shown in FIG. 2A.

The term "(1S, 2R)-norpseudoephedrine", as used herein refers to the chemical compound shown in FIG. 2B.

The term "(1R, 2R)-norephedrine" as used herein refers to the chemical compound shown in FIG. 2C.

The term "(1S, 2S)-pseudonorephedrine", as used herein refers to the chemical compound shown in FIG. 2D.

The term "(1R, 2S)-ephedrine", as used herein refers to the chemical compound shown in FIG. 2E.

The term "(1S, 2R)-pseudoephedrine", as used herein refers to the chemical compound shown in FIG. 2F.

The term "(1R, 2R)-ephedrine", as used herein refers to the chemical compound shown in FIG. 2G.

The term "(1S, 2S)-pseudoephedrine", as used herein refers to the chemical compound shown in FIG. 2H.

The term "(1R, 2S)—N-methylephedrine", as used herein refers to the chemical compound shown in FIG. 2I.

The term "(1S, 2R)—N-methylpseudoephedrine", as used herein refers to the chemical compound shown in FIG. 2J.

The term "(1R, 2R)—N-methylephedrine", as used herein refers to the chemical compound shown in FIG. 2K.

The term "(1S, 2S)—N-methylpseudoephedrine" as used herein refers to the chemical compound shown in FIG. 2L.

The terms "N-methyltransferase" and "NMT" which may be used interchangeably herein refer to any and all enzymes comprising a sequence of amino acid residues which is (i) substantially identical to the amino acid sequences constituting any N-methyltransferase polypeptide set forth herein, including, for example, SEQ. ID NO: 3, or (ii) encoded by a nucleic acid sequence capable of hybridizing under at least moderately stringent conditions to any nucleic acid sequence encoding any N-methyltransferase polypeptide set forth herein, but for the use of synonymous codons.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil, and xanthine and hypoxanthine.

The term "nucleic acid sequence encoding N-methyltransferase", "nucleic acid sequence encoding a N-methyltransferase polypeptide", refer to any and all nucleic acid sequences encoding a N-methyltransferase polypeptide, including, for example, SEQ. ID NO: 1 and SEQ. ID NO 2. Nucleic acid sequences encoding a N-methyltransferase polypeptide further include any and all nucleic acid sequences which (i) encode polypeptides that are substantially identical to the N-methyltransferase polypeptide sequences set forth herein; or (ii) hybridize to any N-methyltransferase nucleic acid sequences set forth herein under at least moderately stringent hybridization conditions or which would hybridize thereto under at least moderately stringent conditions but for the use of synonymous codons.

By the term "substantially identical" it is meant that two polypeptide sequences preferably are at least 70% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990:215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+]+0.41(% (G+C)-600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "chimeric" as used herein in the context of nucleic acid sequences refers to at least two linked nucleic acid sequences which are not naturally linked. Chimeric nucleic acid sequences include linked nucleic acid sequences of different natural origins. For example a nucleic acid sequences constituting a yeast promoter linked to a nucleic acid sequence encoding a N-methyltransferase polypeptide is considered chimeric. Chimeric nucleic acid sequences also may comprise nucleic acid sequences of the same natural origin, provided they are not naturally linked. For example a nucleic acid sequence constituting a promoter obtained from a particular cell-type may be linked to a nucleic acid sequence encoding a polypeptide obtained from that same cell-type, but not normally linked to the nucleic acid sequence constituting the promoter. Chimeric nucleic acid sequences also include nucleic acid sequences comprising any naturally occurring nucleic acid sequences linked to any non-naturally occurring nucleic acid sequence.

The terms "substantially pure" and "isolated", as may be used interchangeably herein describe a compound, e.g., ephedrine or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with an enzyme or protein or ephedrine, or a related alkaloid compound, refers to a more or less pure form of the enzyme or ephedrine or a related alkaloid compound.

The term "in vivo" as used herein to describe methods of making ephedrine or related alkaloid compounds refers to contacting a first chemical compound with an enzyme capable of catalyzing a conversion of the compound within a living cell, including, for example, a microbial cell or a plant cell, to form ephedrine or a related alkaloid compound.

The term "in vitro" as used herein to describe methods of making ephedrine or related alkaloid compounds refers to contacting a first chemical compound with an enzyme capable of catalyzing conversion of the compound in an environment outside a living cell, including, without limitation, for example, in a microwell plate, a tube, a flask, a beaker, a tank, a reactor and the like, to form ephedrine or a related alkaloid compound.

The term "halogen", as used herein, refers to an atom of chlorine, bromine, fluorine, or iodine.

The term "methyl-donor" as used herein refers to a compound or molecule which can transfer a methyl ($CH_3$) group to an alkaloid compound of formula (I) resulting in an alkaloid compound of formula (II).

It should be noted that terms of degree such as "substantially", "essentially" "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

All publications, patents and patent applications are herein incorporated by reference in their entirety to the same extent as if each individual publication.

General Implementation

In one implementation, in accordance herewith there is provided, a method of making an alkaloid compound having a chemical formula (II):

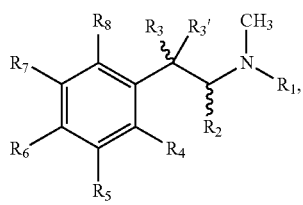
(II)

the method comprising
providing an alkaloid compound having a chemical formula (I):

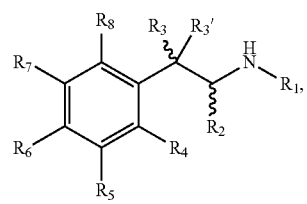
(I)

contacting the alkaloid compound having a chemical formula (I) with sufficient quantities of a methyl-donor and a catalytic quantity of an N-methyl-transferase under reaction conditions permitting an enzyme-catalyzed conversion of the alkaloid compound having chemical formula (I) to an alkaloid compound having chemical formula (II).

In some implementations, in the alkaloid compound having chemical formula (I) $R_1$ is a hydrogen atom, a methyl group or a halogen; $R_2$ is a hydrogen atom, a methyl group or a methoxy group; $R_3$ is a hydroxyl group or a halogen, $R_3'$ is a hydrogen atom, or taken together $R_3$ and $R_3'$ form a carbonyl group (C=O); $R_4$-$R_8$ are each independently or simultaneously a hydrogen atom, methyl group, hydroxyl group, halogen or methoxy group; and each $R_1$ to $R_8$ and $R_3'$ in the alkaloid compound having chemical formula (I) are identical to $R_1$ to $R_8$ and $R_3'$ in the alkaloid compound having chemical formula (II). $R_3$ halogen groups include chlorine, fluorine, bromine and iodine.

In one implementation, the present disclosure provides a method of making an alkaloid compound having a chemical formula (II):

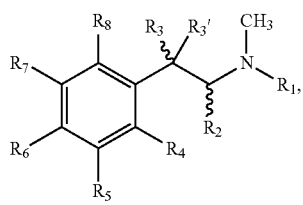
(II)

the method comprising providing an alkaloid compound having a chemical formula (I):

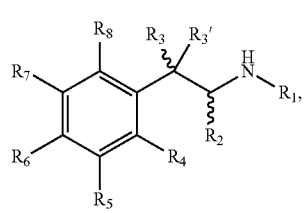
(I)

contacting the alkaloid compound having a chemical formula (I) with sufficient quantities of a methyl-donor and a catalytic quantity of an N-methyl-transferase under reaction conditions permitting an enzyme catalyzed conversion of the alkaloid compound having chemical formula (I) to an alkaloid compound having chemical formula (II), wherein $R_1$ is a hydrogen atom, a methyl group or a halogen; $R_2$ is a hydrogen atom, a methyl group or a methoxy group; $R_3$ is a hydroxyl group or a halogen, $R_3'$ is a hydrogen atom, or taken together $R_3$ and $R_3'$ form a carbonyl group (C=O); $R_4$-$R_8$ are each independently or simultaneously a hydrogen atom, methyl group, hydroxyl group, halogen or methoxy group; and each $R_1$ to $R_8$ and $R_3'$ in the alkaloid compound having chemical formula (I) are identical to $R_1$ to $R_8$ $R_3'$ in the alkaloid compound having chemical formula (II).

In some implementations, in both the alkaloid compound having chemical formula (I) and the alkaloid compound having chemical formula (II), $R_1$ is a hydrogen atom, $R_2$ is a methyl group, $R_3$ is a hydroxyl group, $R_3'$ is a hydrogen atom, and $R_4$-$R_8$ are hydrogen atoms. It is noted that in such implementations, the alkaloid compound having chemical formula (I) is also referred to as norephedrine and the alkaloid compound having chemical formula (II) is also referred to as ephedrine.

In some implementations, in both the alkaloid compound having chemical formula (I) and the alkaloid compound having chemical formula (II) $R_1$ is a methyl group, $R_2$ is a methyl group, $R_3$ is a hydroxyl group, $R_3'$ is hydrogen atom and $R_4$-$R_8$ are hydrogen atoms. It is noted that in such implementations, the alkaloid compound having chemical formula (I) is also referred to as ephedrine and the alkaloid compound having chemical formula (II) is also referred to as N-methylephedrine.

In some implementations, $R_2$ is spatially oriented so that the alkaloid compound having a chemical formula (I) or (II) is a 2R-enantiomer.

In some implementations, $R_2$ is spatially oriented so that the alkaloid compound having a chemical formula (I) or (II) is a 2S-enantiomer.

In some implementations, $R_3$ is spatially oriented so that the alkaloid compound having a chemical formula (I) or (II) is a 1R-enantiomer.

In some implementations, $R_3$ is spatially oriented so that the alkaloid compound having a chemical formula (I) or (II) is a 1S-enantiomer.

In some implementations, the alkaloid compound having chemical formula (I) is (1S, 2S)-pseudonorephedrine and the alkaloid compound having chemical formula (II) is (1S, 2S)-pseudoephedrine.

In some implementations, the alkaloid compound having chemical formula (I) is (1R, 2R)-norephedrine and the alkaloid compound having chemical formula (II) is (1R, 2R)-ephedrine.

In some implementations, the alkaloid compound having chemical formula (I) is (1R, 2S)-norephedrine and the alkaloid compound having chemical formula (II) is (1R, 2S)-ephedrine.

In some implementations, the alkaloid compound having chemical formula (I) is (1S, 2R)-norpseudoephedrine and the alkaloid compound having chemical formula (II) is (1S, 2R)-pseudoephedrine.

In some implementations, the alkaloid compound having chemical formula (I) is (1S, 2S)-pseudoephedrine and the alkaloid compound having chemical formula (II) is (1S, 2S)—N-methyl-pseudoephedrine.

In some implementations, the alkaloid compound having chemical formula (I) is (1R, 2R)-ephedrine and the alkaloid compound having chemical formula (II) is (1R, 2R)—N-methyl-ephedrine.

In some implementations, the alkaloid compound having chemical formula (I) is (1R, 2S)-ephedrine and the alkaloid compound having chemical formula (II) is (1R, 2S)—N-methyl-ephedrine.

In some implementations, the alkaloid compound having chemical formula (I) is (1S, 2R)-pseudoephedrine and the alkaloid compound having chemical formula (II) is (1S, 2R)—N-methyl-pseudoephedrine.

In some implementations, in both the alkaloid compound having chemical formula (I) and (II) $R_1$, and $R_4$-$R_8$ are each hydrogen atoms, $R_2$ is methyl and $R_3$ and $R_3'$ taken together form a carbonyl group (C=O). It is noted that the compound having chemical formula (I) is known as cathinone, and the compound having chemical formula (II) is known as methcathinone. In some implementations, the alkaloid compound having chemical formula (I) is (S)-cathinone and the alkaloid compound having chemical formula (II) is (S)-methcathinone. In some implementations, the alkaloid compound having chemical formula (I) is (R)-cathinone and the alkaloid compound having chemical formula (II) is (R)-methcathinone.

In some implementations, in both the alkaloid compound having chemical formula (I) and (II), $R_1$, $R_2$, $R_3'$ $R_4$, $R_5$, $R_7$ and $R_8$ are each hydrogen atoms, and $R_3$ and $R_6$ are hydroxyl groups. It is noted that the compound having chemical formula (I) is known as p-octopamine, and the compound having chemical formula (II) is known as synephrine.

In some implementations, in both the alkaloid compound having chemical formula (I) and (II), $R_1$ is a methyl group, $R_2$, $R_3'$, $R_4$, $R_5$, $R_6$ and $R_8$ are each hydrogen atoms, and $R_3$ and $R_7$ are hydroxyl groups. It is noted that the compound having chemical formula (I) is known as N-desmethylphenylephrine, and the compound having chemical formula (II) is known as phenylephrine.

In some implementations, in both the alkaloid compound having chemical formula (I) and (II), $R_1$ is a methyl group, $R_2$, $R_3'$, $R_4$, $R_5$, $R_7$ and $R_8$ are each hydrogen atoms, and $R_3$ and $R_6$ are hydroxyl groups. It is noted that the compound having chemical formula (I) is known as synephrine, and the compound having chemical formula (II) is known as N-methylsynephrine.

In some implementations, the alkaloid compound having chemical formula (I) is selected from the group of compounds consisting of 3'-chloro-2-aminopropiophenone; normephedrone; normethedrone; oxidopamine; m-tyramine; amphetamine; noradrenaline; normetraminol; gepefrine; dopamine, p-tyramine; p-octopamine; phenylethanolamine (β-hydroxy phenylethanolamine); 2-phenethylamine; ortetamine; β-methyl-phenethylamine; 3-methoxy-tyramine; normethoxyphenamine; mescaline, 3,4dimethoxyphenethylamine; normacromerine; and S-methcathinone.

In Vitro Synthesis

In accordance with certain aspects of the present disclosure, an alkaloid compound having a chemical formula (I) is brought in contact with sufficient quantities of a methyl-donor and catalytic quantities of an N-methyltransferase under reaction conditions permitting an enzyme catalyzed chemical conversion of an alkaloid compound having chemical formula (I) to an alkaloid compound having chemical formula (II) under in vitro reaction conditions. Under such in vitro reaction conditions the initial reaction constituents are provided in more or less pure form and are contacted with each other and mixed under conditions that permit the requisite chemical reactions, upon enzyme catalysis, to substantially proceed. Substantially pure forms of the initial alkaloid compound having a chemical formula (I) may be chemically synthesized or isolated from natural sources, including from plant species belonging to the genus Khat and plant species belonging to the genus *Ephedra*. Suitable plant species include, without limitation, *Catha edulis, Ephedra sinica* and *Ephedra distachya*

In accordance herewith, more or less pure forms of the enzymes may be isolated from natural sources, microbial species, and the hereinbefore mentioned plant species, or they may be prepared recombinantly. Thus, provided herein is further a method for preparing an N-methyltransferase comprising:

(a) providing a chimeric nucleic acid sequence comprising as operably linked components:
  (i) one or more nucleic acid sequences encoding an N-methyltransferase; and
  (ii) one or more nucleic acid sequences capable of controlling expression in a host cell;
(b) introducing the chimeric nucleic acid sequence into a host cell and growing the host cell to produce an N-methyltransferase; and
(c) recovering the N-methyltransferase from the host cell.

In preferred implementations, the N-methyltransferase is a polypeptide obtainable or obtained from a plant belonging to a plant genus selected from the group consisting of *Ephedra, Catha, Sesamum, Brassica* and *Erythranthe*. In particularly preferred implementations, the N-methyltransferase is a polypeptide obtainable or obtained from a plant species selected from the group consisting of *Ephedra sinica, Catha edulis, Sesamum indicum, Brassica rapus* and *Erythranthe guttata*.

In preferred implementations, the N-methyltransferase is a polypeptide having a polypeptide sequence represented by SEQ. ID NO: 3, SEQ. ID NO: 5; SEQ. ID NO: 7 or SEQ. ID NO: 9.

Growth of the host cells leads to production of the N-methyltransferase. The polypeptides subsequently may be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus substantially pure preparations of the N-methyltranferase polypeptides may be obtained.

In accordance herewith, an alkaloid compound having chemical formula (I) is brought in contact with sufficient quantities of a methyl-donor and catalytic quantities of N-methyl transferase under reaction conditions permitting an enzyme catalyzed chemical conversion of the alkaloid compound having chemical formula (I) to an alkaloid compound having chemical formula (II). A variety of methyl-donors may be used. In preferred embodiments, S-adenosyl methionine (SAM) is used as a methyl-donor. In other embodiments other methyl donors are used including, natural or synthetic methyl-donors, including, without limitation, L-methionine; L-methionine ethyl ester (MEE); methyl ester of methionine (MME); N-derivatized methionine analogues, such as N-acetyl-L-methionine (NAM), and N,N-dimethyl-L-methionine (DMM); aziridinium-based SAM analogues; SAM analogues comprising a substituted L-methyl-group, for example, a terminal alkynyl, keto or amino group; or S/Se-Met analogues. Further reference to these and other methyl donors that may be used in accordance herewith can be found in Biochemistry (2014) 53:1521-1526; Microbiology (2015) 161 (Pt 3):674-682; Agnew. Chem. Int. Ed. (2014) 53:3965-3969; Nature Chemical Biology (2006) 2:31-32; Org. Biomol. Chem. (2013) 11:7606-7610; and Anal. Biochem. (2014) 450:11-19. The quantities of methyl-donor that are used may vary. In some implementations, equimolar, or approximately equimolar amounts of a methyl-donor and an alkaloid compound having chemical formula (I) are provided. In some implementations, the methyl-donor is provided in excess of an equimolar quantity of and an alkaloid compound having chemical formula (I).

In some implementations, the agents are brought in contact with each other and mixed to form a mixture. In some implementations, the mixture is an aqueous mixture comprising water and further optionally additional agents to facilitate enzyme catalysis, including buffering agents, salts, pH modifying agents, or other enzymes. The reaction may be performed at a range of different temperatures. In preferred implementations, the reaction is performed at a temperature between about 18° C. and 37° C. Upon completion of the in vitro reaction and an alkaloid compound having chemical formula (II) may be obtained in more or less pure form.

In Vivo Synthesis

In accordance with certain aspects of the present disclosure, an alkaloid compound having a chemical formula (I) is brought in contact with sufficient quantities of a methyl-donor and catalytic quantities of an N-methyltransferase under reaction conditions permitting an enzyme catalyzed chemical conversion of an alkaloid compound having chemical formula (I) to an alkaloid compound having chemical formula (II) under in vivo reaction conditions. Under such in vivo reaction conditions living cells are modified in such a manner that they produce an alkaloid compound having chemical formula (II). In certain implementations, the living cells are microorganisms, including bacterial cells and fungal cells. In other embodiments, the living cells are multicellular organisms, including plants.

In one implementation, the living cells are selected to be host cells capable of producing an alkaloid compound having chemical formula (I), but not an alkaloid compound having chemical formula (II). Such cells include, without limitation, bacteria, yeast, other fungal cells, plant cells, or animal cells. Thus, by way of example only, a host cell may be a yeast host cell capable of producing cells capable of producing an alkaloid compound having chemical formula (I), but not an alkaloid compound having chemical formula (II).

In some implementations, such a host cell, a yeast cell, for example, is used which is capable of producing one or more of the following compounds serving as a precursor to the alkaloid compound having chemical formula (I): (1R)-phenylacetylcarbinol (R-PAC), (1S)-phenylacetylcarbinol (S-PAC), (S)-cathione, 1 phenylpropane-1,2-dione, benzoyl-CoA, benzaldehyde or benzoic acid, such a cell not being capable of producing an alkaloid compound having chemical formula (II). In some implementations, one or more of the compounds (1R)-phenylacetylcarbinol (R-PAC), (1S)-phenylacetylcarbinol (S-PAC), (S)-cathione, 1 phenylpropane-1,2-dione, benzoyl-CoA, benzaldehyde or benzoic acid serving as a precursor compound to the alkaloid compound having chemical formula (I) is synthesized by a cell exogenously supplemented with benzaldehyde. In order to modulate such host cells in such a manner that they produce an alkaloid compound having chemical formula (II), an N-methyltransferase in accordance herewith may be heterologously introduced and expressed in the host cells.

In some implementations, the host cells comprise one or more enzymes capable of producing an alkaloid compound having chemical formula (I) and/or a precursor thereof.

In some implementations, the host cells comprises a reductase capable of catalyzing a reaction resulting in the production of norephedrine from (S)-cathinone.

In some implementations, the host cell comprises a transaminase capable of catalyzing a reaction resulting in the production of norephedrine from (1R)-phenylacetylcarbinol (R-PAC), (1S)-phenylacetylcarbinol (S-PAC).

In some implementations, the host cell comprises transaminase capable of catalyzing a reaction resulting in the production of (S)-cathione from 1-phenyl-propane-1,2-dione.

In some implementations, the host cell comprises a carboligase capable of catalyzing a reaction resulting in the production of (1R)-phenylacetylcarbinol (R-PAC), (1S)-phenylacetylcarbinol (S-PAC) from benzaldehyde.

In some implementations, the host cell comprises a carboligase capable of catalyzing a reaction resulting the production of 1-phenyl-propane-1,2-dione from benzoyl-CoA.

In some implementations, the host cell comprises a CoA-ligase capable of catalyzing a reaction resulting in the production of benzoyl-CoA from benzoic acid.

In some implementations, the host cell comprises a dehydrogenase capable of catalyzing a reaction resulting in the production of benzoic acid from benzaldehyde.

In other embodiments, the living cells naturally produce an alkaloid compound having chemical formula (II), however the living cells are modulated in such a manner that the level of an alkaloid compound having chemical formula (II) produced is modulated, relative to the level produced by the cell without heterologous introduction of any of the aforementioned enzymes in such living cells.

In order to produce alkaloid compound having chemical formula (II), provided herein is further a method for preparing an alkaloid compound having chemical formula (II) comprising:
 (a) providing a chimeric nucleic acid sequence comprising as operably linked components:
  (i) a nucleic acid sequence encoding an N-methyltransferase polypeptide; and
  (ii) one or more nucleic acid sequences capable of controlling expression in a host cell;
 (b) introducing the chimeric nucleic acid sequence into a host cell and growing the host cell to produce the N-methyltransferase and to produce the alkaloid compound having chemical formula (II); and
 (c) recovering the alkaloid compound having chemical formula (II).

In some implementations, the nucleic acid sequences may be isolated from the hereinbefore mentioned plant species. In some implementations, the nucleic acid sequences are selected from the nucleic acid sequences set forth herein as one SEQ. ID NO: 1, SEQ. ID NO: 2, SEQ. ID NO: 4, SEQ. ID NO: 6 or SEQ. ID NO: 8.

In accordance herewith, the nucleic acid sequence encoding N-methyltransferase is linked to a nucleic acid sequence capable of controlling expression of N-methyltransferase in a host cell. Accordingly, the present disclosure also provides a nucleic acid sequence encoding N-methyltransferase linked to a promoter capable of controlling expression in a host cell. Nucleic acid sequences capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further nucleic acid elements capable elements of controlling expression in a host cell include transcriptional terminators, enhancers and the like, all of which may be included in the chimeric nucleic acid sequences of the present disclosure.

In accordance with the present disclosure, the chimeric nucleic acid sequences comprising a promoter capable of controlling expression in host cell linked to a nucleic acid sequence encoding an N-methyltransferase, can be integrated into a recombinant expression vector which ensures good expression in the host cell. Accordingly, the present disclosure includes a recombinant expression vector comprising as operably linked components:

(i) a nucleic acid sequence capable of controlling expression in a host cell; and (ii) a nucleic acid sequence encoding an N-methyltransferase, wherein the expression vector is suitable for expression in a host cell. The term "suitable for expression in a host cell" means that the recombinant expression vector comprises the chimeric nucleic acid sequence of the present disclosure linked to genetic elements required to achieve expression in a host cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

One host cell that particularly conveniently may be used is *Escherichia coli*. The preparation of the *E. coli* vectors may be accomplished using commonly known techniques such as restriction digestion, ligation, gelectrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Further included in the present disclosure are a host cell wherein the host cell comprises a chimeric nucleic acid sequence comprising in the 5' to 3' direction of transcription as operably linked components one or more nucleic acid sequences encoding an N-methyltransferase. As hereinbefore mentioned the host cell is preferably a host cell capable of producing an alkaloid compound having chemical formula (I), but is unable to produce an alkaloid compound having chemical formula (II), but for the introduction of the chimeric nucleic acid sequences of the present disclosure.

As hereinbefore mentioned, in other embodiments, the host cells naturally produce an alkaloid having chemical formula (II), however the host cells are modulated in such a manner that the levels of an alkaloid having chemical formula (II) produced in the cells is modulated, relative to levels of such alkaloid produced by the cell without heterologous introduction of any of the aforementioned enzymes in such host cells. Such modulations may be achieved by a variety of modification techniques, including, but not limited to, the modulation of the enzymatic activity of an N-methyltransferase, for example by modulating the native nucleic acid sequences encoding the N-methyltransferase, for example by gene silencing methodologies, such as antisense methodologies; or by the use of modification techniques resulting in modulation of activity of the enzymes using for example site directed mutagenesis, targeted mutagenesis, random mutagenesis, virus-induced gene silencing, the addition of organic solvents, gene shuffling or a combination of these and other techniques known to those of skill in the art, each methodology designed to alter the activity of the enzymes of the N-methyltransferase, in such a manner that level of alkaloid compound having chemical formula (II) in the host cells increases.

EXAMPLES

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

Example 1—Ephedrine, Norephedrine, Pseudoephedrine, Cathinone, Synephrine and Octopamine as Substrates for *Escherichia coli* and *Ephedra sinica* Produced N-Methyltransferase This example describes the use ephedrine and five other related chemical compounds as substrates for N-methyltransferase. The N-methyltransferase is obtained from a plant belonging to the genus *Ephedra*, notably *Ephedra sinica*, and expressed in microbial host cells, notably *Escherichia coli*. This example further describes the use of an N-methyltransferase obtained from *Ephedra sinica* using norephedrin as a substrate.

Construct Assembly and Protein Expression in *E. coli*.

Open reading frames (ORFs) of N-methyltransferase (NMT) enzyme sequences (i.e. SEQ. ID NO: 1 and SEQ. ID NO: 2) were subcloned into *Escherichia coli* expression vector pET47b (Merck Millipore) in-frame with vector-encoded His-tag for downstream purification purposes. Constructs were transformed into *E. coli* strains ArcticExpress (Agilent Technologies) or Rosetta (Novagen). Recombinant His-tagged protein production was performed according to standard procedures (Farrow et al. 2013. J. Biol. Chem. 288: 28977) and manufacturer's instructions. Briefly, cultures of *E. coli* harboring pET47b were grown on an orbital shaker (200 rpm) to log phase in 1 L of LB medium containing gentamicin, streptomycin and kanamycin (Arctic Express) or chloramphenicol and kanamycin (Rosetta). Recombinant His-tagged protein production was initiated by the addition of 1 mM isopropyl β-D-1-thiogalactopyranoside (IPTG). To produce NMT, cultures were grown for 24 h at 15° C.

Enzyme Purification and Activity Assays.

For purification, bacterial pellets obtained following induction/incubation were resuspened in 10 mL of resuspension buffer (50 mM Tris pH 8.5, 10% v/v glycerol, 1% w/v polyvinylpyrrolidone, 5 mM dithiothreitol) and lysed at 4° C. using a French pressure cell (1,000 psi). After centrifugation (10,000 g) to remove insoluble debris, the supernatant was incubated on ice with buffer-equilibrated Talon resin (Clontech) on an orbital shaker (60 rpm) for 60 minutes. The protein-charged resin was washed twice with 10 mL of cold resuspension buffer containing 2.5 mM imidazole, and proteins were eluted stepwise with increasing concentrations (10 to 200 mM) of imidazole in resuspension buffer. Total proteins from a 40 mM imidazole elution were desalted using a PD-10 column (EMD Millipore) and resuspension buffer free of imidazole. Recombinant proteins were analyzed by SDS-PAGE to assess yield and purity, and immunoblot analyses were conducted using α-His primary antibodies and goat-anti-mouse, horseradish peroxidase-conjugated secondary antibodies. Total protein concentration was determined using BCA Protein Assay kit (Thermo Scientific). Calculated protein concentrations were adjusted on gel densitometry. Standard enzyme assays included approximately 100 µg/mL purified NMT protein, which was determined to be in the linear range of catalyst performance. Specifically, standard enzyme reactions consisted of 50 mM Tris pH 8.5, 10 v/v glycerol, 1% w/v polyvinylpyrrolidone, 5 mM dithiothreitol, 1 mM alkaloid substrate, 1 mM SAM (S-adenosylmethionine) and 100 µg/mL purified NMT protein in a total of 100 µl reaction volume. Reactions were incubated for 4 h at 37° C., and stopped via 1) basification of the reaction mixture to pH 10-11, and 2) immediate addition of 1 mL ethyl acetate. Quenched reactions were vortexed and centrifuged (10,000 rpm) to separate organic and aqueous phases, and organic phase was carefully drawn off, placed in a new tube, reduced to dryness under vacuum, and resuspended in 500 µL of Solvent A (10 mM ammonium acetate pH 5.5, 5% v/v methanol). The resuspensions were centrifuged (10,000 rpm) prior to analysis by LC-MS to remove insoluble matter.

Liquid Chromatography-Mass Spectrometry (LC-MS) Analysis

Ten µL sample was injected for LC-MS analysis using an Agilent 6410B triple quadrupole mass analyzer equipped with a 1200 Agilent HPCL system. Samples were fractionated using a previously described LC-ESI-MS/MS method [J. Chromatography B. 879:727, 2011] employing a Prodigy Phenyl-3 column (Phenomenex) which separated enantiomeric pairs (e.g. pseudoephedrine/ephedrine). Briefly, the HPLC gradient began as 95% Solvent A (Solvent B=100% methanol) for 1 minute at a flow rate of 0.2 ml/min, and decreased to 30% Solvent A/70% Solvent B over 19 minutes, then graded to 10% Solvent A/90% Solvent A over 0.5 minutes, then immediately returned to 100% Solvent A and equilibrated for 5 minutes. Retention times (minutes) were as follows: norephedrine=4.3; ephedrine=6.9; pseudoephedrine=7.9; cathinone=7.1; methylephedrine=10.6; methylpseudoephedrine=11.9; methcathinone=10.1. ESI and MS conditions were essentially the same as described [J. Chromatography B. 879:727, 2011]. Briefly, the MS was operated in positive ion mode with probe voltage of 4000 V and an extractor potential of 3 V, dwell time of 200 ms for all transitions, and CID spectra were acquired for product identification. Nitrogen was used for CID analyses. CID spectra and retention times of enzyme products were compared with those of authentic standards. Additional comparisons were made with published values [J. Chromatography B. 879:727, 2011; http://www.massbank.jp]. Enzyme activity was measured by integrating total area under product peaks of TIC (total ion count) spectra. Control samples consisting of boiled enzyme yielded negligible product. MS data analysis was performed using MassHunter Workstation software (Agilent), and subsequent enzyme activity calculations were performed manually with the aid of Microsoft Excel (Microsoft Corporation).

Analysis of *Ephedra sinica* Plant Tissue.

For comparative purposes, 2.0 grams of *Ephedra sinica* plant tissue was analyzed for NMT activity according to the protocol of Krizevski et al. [Phytochemistry 71:895, 2010]. Briefly, the tips of the young shoots (5 cm from the tip inward) were harvested from 2-year old *E. sinica* plants and ground to fine powder in a mortar and pestle under liquid nitrogen. The powder was added to cold extraction buffer [50 mM Tris pH 8.5, 10 v/v glycerol, 1% w/v polyvinylpyrrolidone, 5 mM dithiothreitol] and vortexed. Centrifugation (10,000 g) was performed to remove insolubles, and the supernatant was concentrated to 1 mL using an Amicon Ultra Centrifugal filters (10 kD cutoff; Millipore) according to manufacturer's instructions. Several washes were performed using three fresh columns to ensure that all traces of alkaloid present in the plant-derived extraction mixture were removed prior to NMT assay. Assays were performed as described above for enzymes raised in *E. coli* host.

Results

Figure 3:
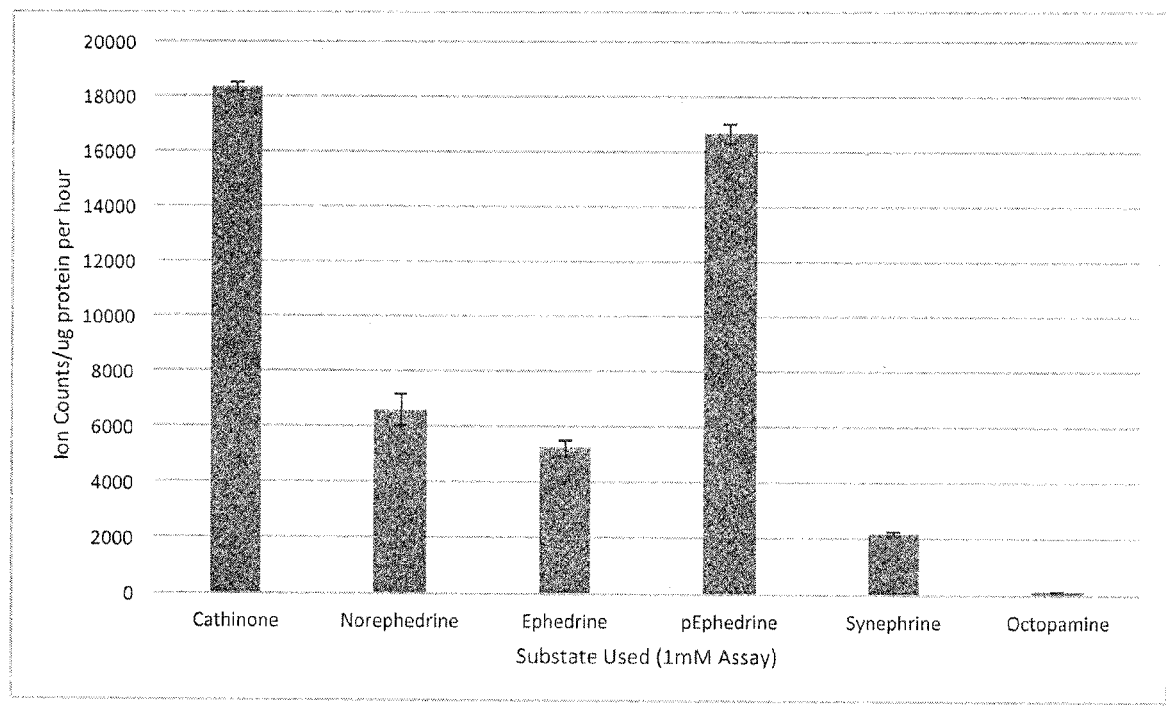
FIG. 3 depicts a bar graph reflecting certain results obtained in the performance of the experiments described in Example 1, notably, the production of N-methylated alkaloids using a variety of substrates under standard assay conditions. Substrates used are listed along the x-axis, and the N-methylated product is quantified as MS ion counts per µg protein per hour. Error bars represent standard deviation (SD) calculated using 4-6 replicates. It is noted that pEphedrine denotes pseudoephedrine.

Expression of native *Ephedra sincia* NMT (SEQ. ID NO: 1) in *E. coli* yielded suboptimal results. Improved expression was observed when a codon-optimized synthetic gene (SEQ. ID NO: 2) was used. Western blotting and SDS-PAGE analysis revealed that expression of this synthetically-encoded NMT was superior using ArcticExpress *E. coli* compared to protein production in Rosetta cells, and therefore all experiments were conducted using the ArticExpress cell line and protocol. Enzyme assays were conducted using a variety of time points and enzyme amounts to determine the linear range of activity. Preliminary results showed that the enzyme activity continued linearly for over 4 hours, and therefore 4 hours was chosen as the time frame of standard assays. Tandem assays conducted with *Ephedra sinica*-derived protein revealed comparable rates of product turnover. As such, 4 hour assays were also conducted for plant-derived enzyme. Norephedrine was used as a substrate for plant-derived extract, yielding ephedrine at comparable levels to *E. coli*-produced NMT under standard assay conditions. Plant-derived NMT assays were conducted as a positive control to ensure that standard assay conditions were adequate for activity. The following substrates were examined in the case of purified, *E. coli*-derived NMT: ephedrine, norephedrine, pseudoephedrine, cathinone, synephrine and octopamine. Results, as shown in FIG. 3. It is noted that control samples using identical conditions with the exception that enzyme was boiled for 20 minutes prior to assay initiation did not yield detectable product. The results illustrate that the NMT accepts a broad range of molecules for N-methylation. Thus NMT accepts primary amines (norephedrine) and secondary amines (ephedrine, pseudoephedrine) with amphetamine analogue-type molecular structure (e.g. with a methyl group attached to the alpha carbon). Another amphetamine-type alkaloid acting as substrate included cathinone, which NMT converts to methcathinone. These results indicated that the NMT was able to turnover an alkaloid with a β-keto group in place of a β-hydroxyl. Synephrine and octopamine do not have an amphetamine-type structure, but were accepted as substrates.

Figure 4:
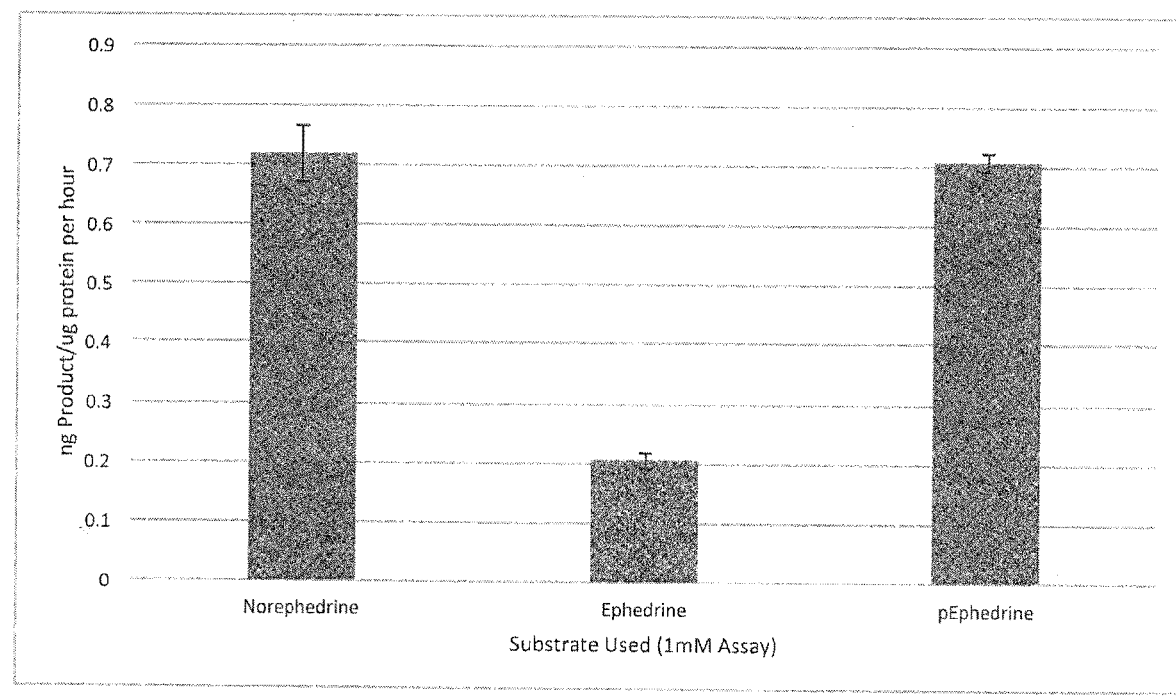
FIG. 4 depicts another bar graph reflecting certain results obtained in the performance of the experiments described in Example 1, notably, the production of N-methylated alkaloids using norephedrine, ephedrine, and pseudoephedrine (pEphedrine) substrates under standard assay conditions. Substrates used are listed along the x-axis, and the N-methylated product is quantified as ng alkaloid per µg protein per hour. Error bars represent standard deviation (SD) calculated using 4-6 replicates The figures together with the following detailed description make apparent to those skilled in the art how the disclosure may be implemented in practice.

In order to enable quantitative comparisons between alkaloids in terms of their effectiveness as substrates, standard curves were prepared for three alkaloids and their N-methylated products. This enabled absolute product quantification in terms of ng of alkaloid. Results shown in FIG. 4 revealed norephedrine to be the preferred NMT substrate, followed closely by pseudoephedrine. The conversion efficiency of ephedrine to N-methylephedrine was somewhat lower. Control samples using identical conditions with the exception that enzyme was boiled for 20 minutes prior to assay initiation did not yield detectable product.

The invention claimed is:

1. A method for preparing an alkaloid compound having chemical formula (II)

$$\text{(II)}$$

the method comprising:
(a) providing a heterologous chimeric nucleic acid comprising as operably linked components:
  (i) a nucleic acid encoding an N-methyltransferase polypeptide comprising a polypeptide selected from the amino acid sequence of SEQ ID NO: 3, SEQ ID NO: 5, SEQ ID NO: 7, and SEQ ID NO: 9, or a polypeptide sequence having at least 85% identity to the amino acid sequence of SEQ ID NO: 3, SEQ ID NO: 5, SEQ ID NO: 7 or SEQ ID NO: 9;
  (ii) one or more nucleic acids capable of controlling expression in a host cell;
(b) introducing the heterologous chimeric nucleic acid into a host cell and growing the host cell to produce the N-methyltransferase and to produce an alkaloid compound having chemical formula (I);

$$\text{(I)}$$

(c) enzymatically catalyzing the conversion of the alkaloid compound having chemical formula (I) to an alkaloid compound having chemical formula (II); and
(d) recovering the alkaloid compound having chemical formula (II); wherein $R_1$ is a hydrogen atom, a methyl group or a halogen; $R_2$ is a hydrogen atom, a methyl group or a methoxy group; $R_3$ is a hydroxyl group or a halogen, $R_3'$ is a hydrogen atom, or taken together $R_3$ and $R_3'$ form a carbonyl group (C=O); and $R_4$-$R_8$ are each independently or simultaneously a hydrogen atom, methyl group, hydroxyl group, halogen or methoxy group and wherein each $R_1$ to $R_8$ and $R_{3'}$ in the alkaloid compound having chemical formula (I) are identical to $R_1$ to $R_8$ and $R_{3'}$ in the alkaloid compound having chemical formula (II).

2. The method of claim 1, wherein the nucleic acid encoding an N-methyltransferase polypeptide is selected from the group consisting of the nucleic acid sequence of SEQ ID NO: 1, SEQ ID NO: 2, SEQ ID NO: 4, SEQ ID NO: 6, and SEQ ID NO: 8.

3. The method of claim 1, wherein the nucleic acid encoding an N-methyltransferase polypeptide is selected from a nucleic acid having at least 85% sequence identity to the nucleic acid sequence of SEQ ID NO: 1, SEQ ID NO: 2, SEQ ID NO: 4, SEQ ID NO: 6, and SEQ ID NO: 8.

4. The method of claim 1, wherein the nucleic acid encodes an N-methyltransferase polypeptide having at least 95% identical to the amino acid sequence of SEQ ID NO: 3, SEQ ID NO: 5, SEQ ID NO: 7, or SEQ ID NO: 9.

5. The method of claim 1, wherein in both the alkaloid compound having chemical formula (I) and the alkaloid compound having chemical formula (II), $R_1$ is a hydrogen atom or methyl group, $R_2$ is a methyl group, $R_3$ is a hydroxyl group, $R_3'$ is a hydrogen atom and $R_4$-$R_8$ are hydrogen atoms.

6. The method of claim 1, wherein $R_2$ is spatially oriented so that the alkaloid compound having a chemical formula (I) or (II) is a 2R-enantiomer.

7. The method of claim 1, wherein $R_2$ is spatially oriented so that the alkaloid compound having a chemical formula (I) or (II) is a 2S-enantiomer.

8. The method of claim 1, wherein $R_3$ is spatially oriented so that the alkaloid compound having a chemical formula (I) or (II) is a 1R-enantiomer.

9. The method of claim 1, wherein $R_3$ is spatially oriented so that the alkaloid compound having a chemical formula (I) or (II) is a 1S-enantiomer.

10. The method of claim 1, wherein the alkaloid compound having chemical formula (I) is (1S, 2S)-pesudo-norephedrine and the alkaloid compound having chemical formula (II) is (1S, 2S)-pesudoephedrine.

11. The method of claim 1, wherein the alkaloid compound having chemical formula (I) is (1R, 2R)-norephedrine and the alkaloid compound having chemical formula (II) is (1R, 2R)-ephedrine.

12. The method of claim 1, wherein the alkaloid compound having chemical formula (I) is (1R, 2S)-norephedrine and the alkaloid compound having chemical formula II) is (1R, 2S)-ephedrine.

13. The method of claim 1, wherein the alkaloid compound having chemical formula (I) is (1S, 2R)-norpseudoephedrine and the alkaloid compound having chemical formula II) is (1S, 2R)-pseudoephedrine.

14. The method of claim 1, wherein the alkaloid compound having chemical formula (I) is (1S, 2S)-pseudoephedrine and the alkaloid compound having chemical formula II) is (1S, 2S)-N-methyl-pseudoephedrine.

15. The method of claim 1, wherein the alkaloid compound having chemical formula (I) is (1R, 2R)- ephedrine and the alkaloid compound having chemical formula (II) is (1R, 2R)-N-methyl-ephedrine.

16. The method of claim 1, wherein the alkaloid compound having chemical formula (I) is (1R, 2S)- ephedrine and the alkaloid compound having chemical formula (II) is (1R, 2S)-N-methyl-ephedrine or the alkaloid compound having formula (I) is (1S, 2R)-pseudoephedrine and the alkaloid compound having chemical formula (II) is (1S, 2R)-N- methyl-pseudoephedrine.

17. The method of claim 1, wherein the N-methyltransferase is a Catha N-methyltransferse or is an Ephedra N-methyltransferase.

* * * * *